(12) United States Patent
Lee et al.

(10) Patent No.: US 7,547,298 B2
(45) Date of Patent: Jun. 16, 2009

(54) LIQUID SAMPLER AND METHOD

(75) Inventors: Helen Hwai-an Lee, Cambridge (GB); Grant Timothy Lewis Smetham, Surrey (GB); Phillip John Stankus, West Sussex (GB); Shaun Christopher Hazlewood, Cambridge (GB); Elipidio Cesar Braga Nadala, San Mateo, CA (US); Craig Alan Wisniewski, Sunnyvale, CA (US)

(73) Assignee: Diagnostics for the Real World, Ltd., Sunnyvale, CA (US)

( * ) Notice: Subject to any disclaimer, the term of this patent is extended or adjusted under 35 U.S.C. 154(b) by 531 days.

(21) Appl. No.: 10/522,609

(22) PCT Filed: Jul. 25, 2003

(86) PCT No.: PCT/GB03/03206

§ 371 (c)(1),
(2), (4) Date: Feb. 21, 2006

(87) PCT Pub. No.: WO2004/010873

PCT Pub. Date: Feb. 5, 2004

(65) Prior Publication Data

US 2006/0149164 A1    Jul. 6, 2006

(30) Foreign Application Priority Data

Jul. 26, 2002    (GB) ................. 0217390.4

(51) Int. Cl.
*A61M 1/00*    (2006.01)

(52) U.S. Cl. .................. 604/319; 604/324; 600/573; 600/574; 600/575

(58) Field of Classification Search ................. 604/319, 604/324; 436/86, 95, 164; 600/573–575
See application file for complete search history.

(56) References Cited

U.S. PATENT DOCUMENTS

| | | | |
|---|---|---|---|
| 3,010,805 A * | 11/1961 | Cheng | ................ 422/252 |
| 3,499,327 A | 3/1970 | Lane | |
| 3,982,898 A | 9/1976 | McDonald | |
| 4,492,258 A | 1/1985 | Lichtenstein et al. | |
| 5,409,473 A | 4/1995 | Rosenshein | |

FOREIGN PATENT DOCUMENTS

| | | | |
|---|---|---|---|
| FR | 2 505 677 | | 11/1982 |
| GB | WO 86/03394 | * | 6/1986 |
| WO | 86/03394 | | 6/1986 |

* cited by examiner

*Primary Examiner*—Tatyana Zalukaeva
*Assistant Examiner*—Ilya Y Treyger
(74) *Attorney, Agent, or Firm*—Proskauer Rose LLP (57) ABSTRACT

In a sampler for sampling a first portion of a liquid flow, the liquid flow enters at a sampler inlet (12). The sample passes through a valve (30) into a sample chamber (8) and then the valve closes, diverting the remainder of the liquid flow to a sampler overflow (6). The valve comprises a valve inlet (24) coupled to the sampler inlet, a valve outlet (38, 36) opening into the sample chamber and positioned, in use, substantially below the valve inlet, a shut-off chamber (32) separating the valve outlet from the valve inlet, and a valve overflow (34) leading from the shut-off chamber to the sampler overflow (6). When the liquid level in the sample chamber rises to a predetermined level it disrupts the flow of liquid through the valve outlet and diverts later flow through the valve inlet into the shut-off chamber and through the valve overflow.

22 Claims, 12 Drawing Sheets

LIQUID SAMPLER AND METHOD

This application is the National Phase of International Application PCT/GB2003/003206, filed Jul. 25, 2003, which designated the U.S., and that International Application was published under PCT Article 21(2) in English as WO 2004/010873, and claims priority to GB 0217390.4, filed Jul. 26, 2002.

This invention relates to a liquid sampler and a method for collecting a liquid sample, and to a diagnostic method comprising the collection of urine.

It is well known that sampling urine can be an effective research and diagnosis tool to investigate an individual's physical condition.

SUMMARY OF INVENTION

The invention provides in a first aspect a liquid sampler and a method for sampling a liquid as defined in the appended independent claims. Preferred or advantageous features of the invention are set out in dependent sub-claims.

As noted above, it is known to perform diagnostic tests on urine samples. In a second aspect of the invention, however, the inventor has appreciated that significant advantages can be achieved and new diagnostic tests implemented if a sample of only the first portion of the urine provided by an individual is tested or investigated. The first urine portion may be termed first-void urine.

There is a problem, however, in isolating first-void urine without excessive dilution by the remainder of the contents of the patient's bladder.

Thus, a preferred embodiment of the first aspect of the invention may advantageously provide a sampler for sampling a first portion of a liquid flow. The liquid flow enters at an inlet of the sampler. The sample passes from the inlet through a valve into a sample chamber and then the valve closes, diverting the remainder of the liquid flow to an overflow or exhaust passage. The valve comprises a valve inlet coupled to the sampler inlet, a valve outlet opening into the sample chamber and positioned, in use, substantially below the valve inlet, a shut-off chamber separating the valve outlet from the valve inlet, and a valve overflow leading out of the shut-off chamber. When the liquid level in the sample chamber rises to a predetermined level it disrupts the flow of liquid through the valve outlet and diverts later flow through the valve inlet into the shut-off chamber and through the valve overflow.

A further embodiment advantageously provides a first-void urine sampler which can be conveniently held by a user while they provide a urine specimen into a funnel, the sampler further comprising a valve which automatically directs a desired volume of first-void urine into a sample chamber and the remainder of the urine specimen to an exhaust passage for disposal.

The urine sampler may thus enable the user to urinate continuously without the need for bladder control or the potentially messy option of moving a collection receptacle out of the urine stream.

Advantageously, the valve provided within the sampler may seal the sample chamber after collection of the first portion of the liquid flow, or the first-void urine, until the sample chamber is removed from the sampler, even if the sampler is tilted or inverted with the sample chamber in place.

In preferred embodiments, the sampler may advantageously collect the first 2 ml to 5 ml or 10 ml of a liquid flow or a urine specimen, although the parameters of the sampler may be varied in order to collect different liquid volumes. The sample collected may also be diluted to a limited degree by liquid or urine delivered later in the liquid flow or the urine specimen. This dilution depends on the speed of operation and the effectiveness of the valve action of the sampler, and may depend on other parameters such as the rate of delivery of the liquid flow or the urine sample.

Clearly, the sampler may find applications in sampling the first portion of any liquid flow. The technique is not limited to urine sampling.

Whilst the invention is mainly directed to (and described with respect to) apparatus and methods suitable for sampling a first portion of a liquid flow (i.e. first-void urine), the apparatus and methods may be employed to collect one or more later samples after a first portion has been collected. Thus, the liquid from the overflow may be collected (all or in part) for any subsequent purpose irrespective of whether or not the first portion sample is desired or simply disposed of. When carrying out diagnostic testing of urine, first-void and later-void urine (e.g. mid-stream urine) may be collected and any or all samples may be tested.

DESCRIPTION OF SPECIFIC EMBODIMENTS AND BEST MODE

Specific embodiments of the invention will now be described by way of example, with reference to the accompanying drawings, in which.

Figure 1:
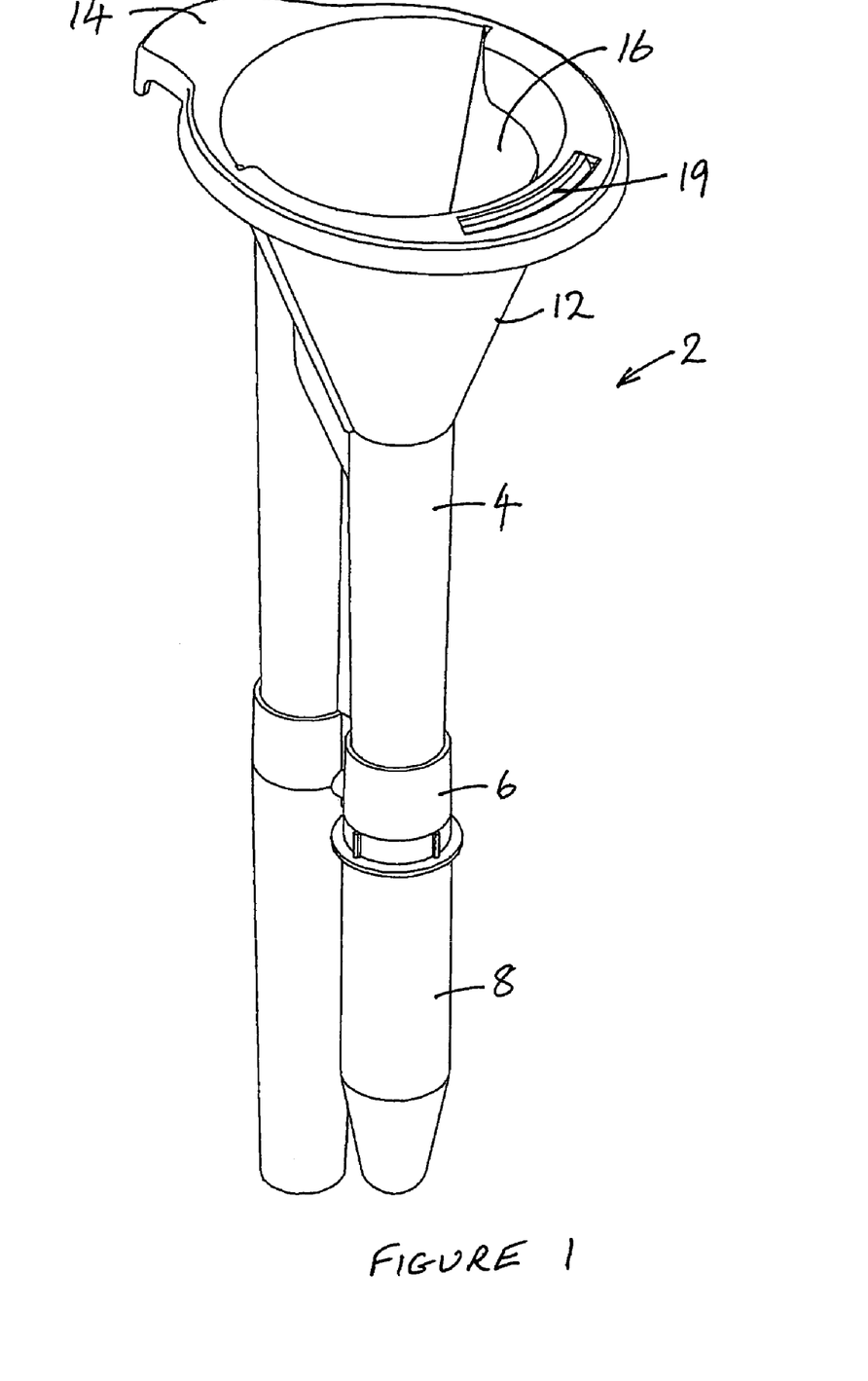
FIG. 1 is a three-quarter view of a urine sampler embodying the invention.
Figure 2:
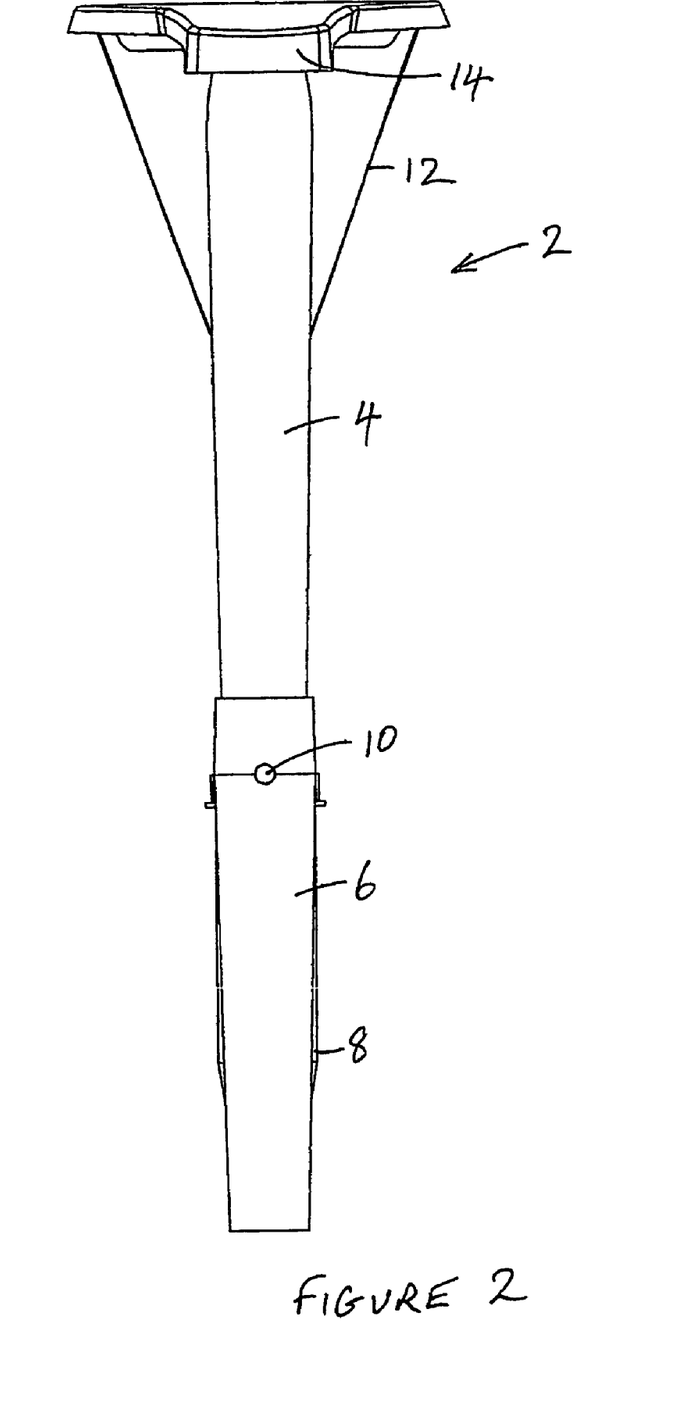
FIG. 2 is a back view of the sampler of FIG. 1.
Figure 3:
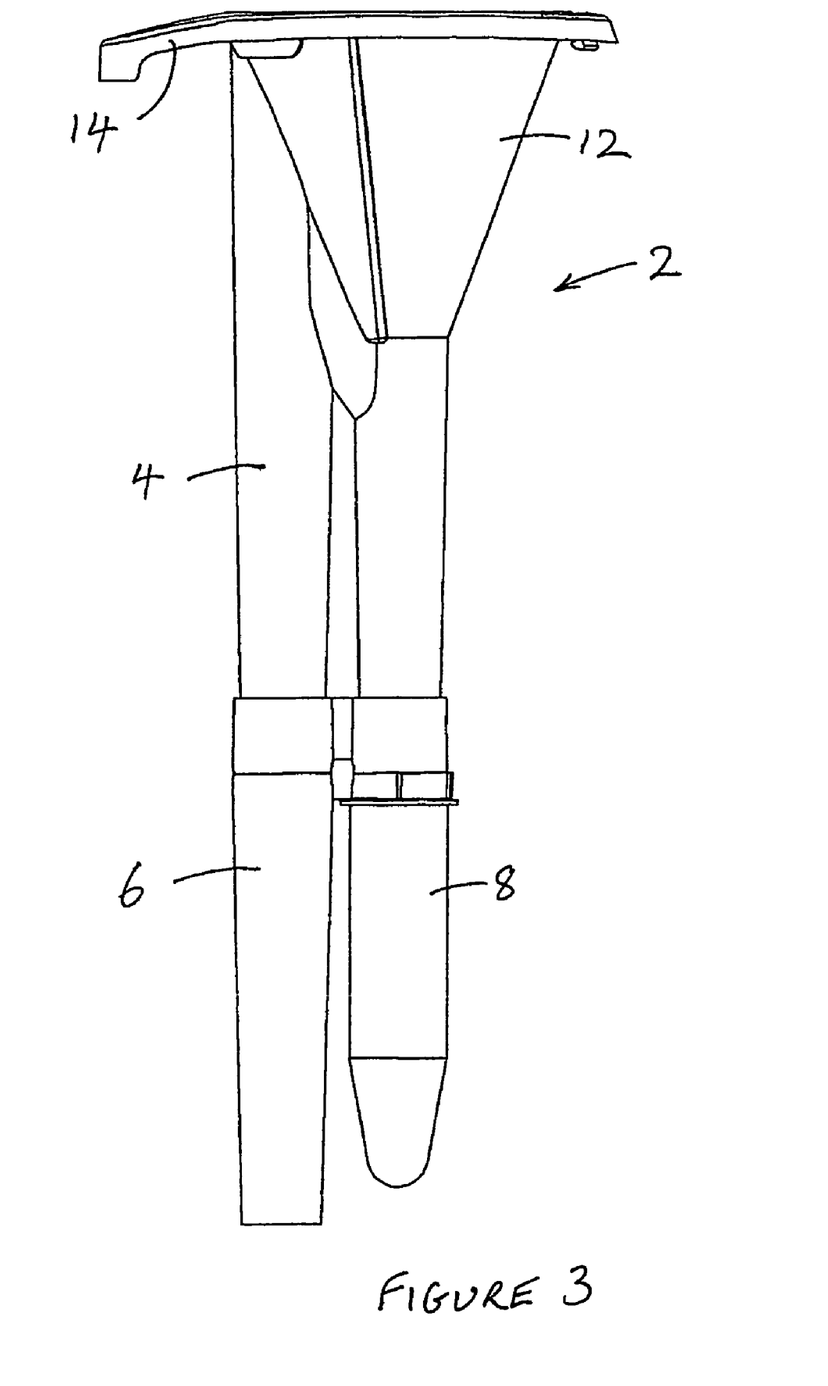
FIG. 3 is a left side view of the sampler of FIG. 1.
Figure 4:
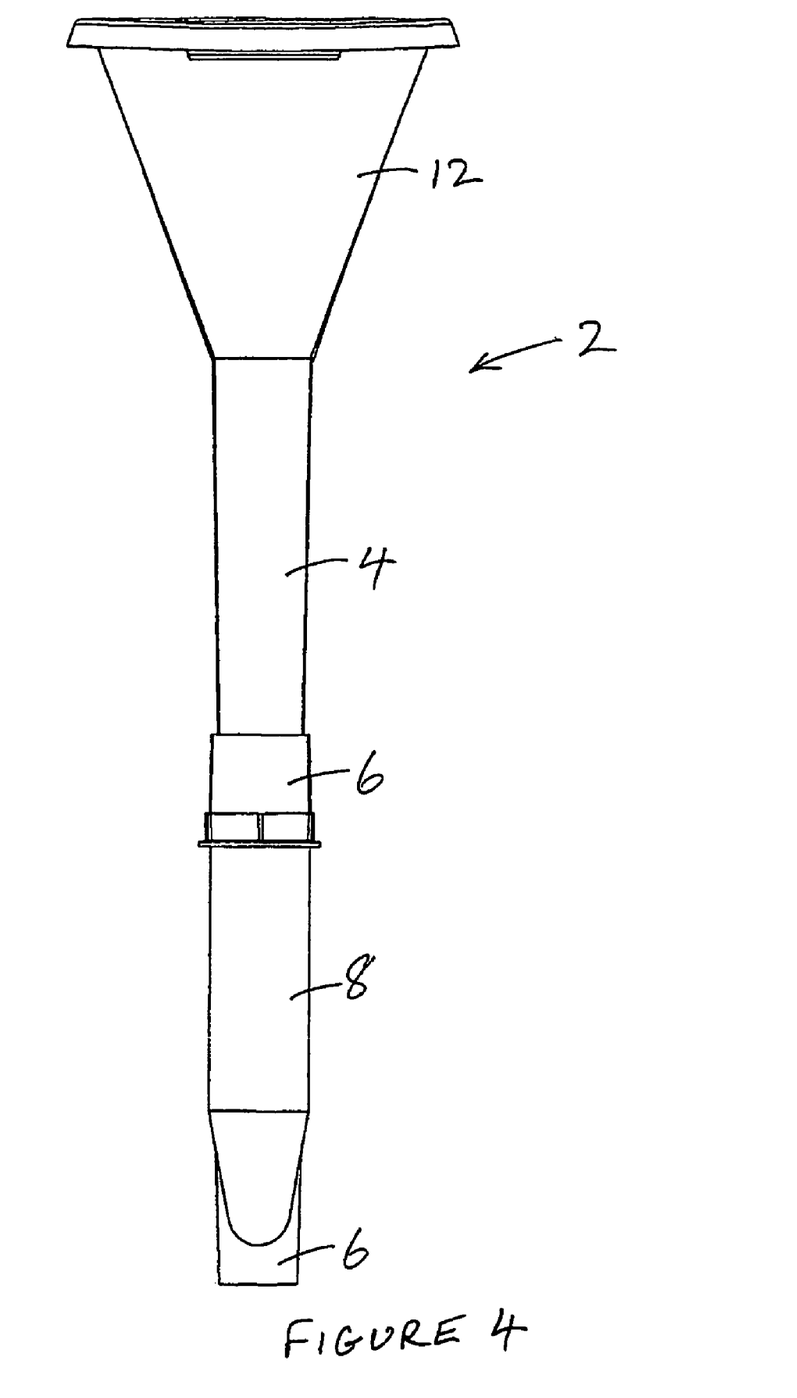
FIG. 4 is a front view of the sampler of FIG. 1.
Figure 5:
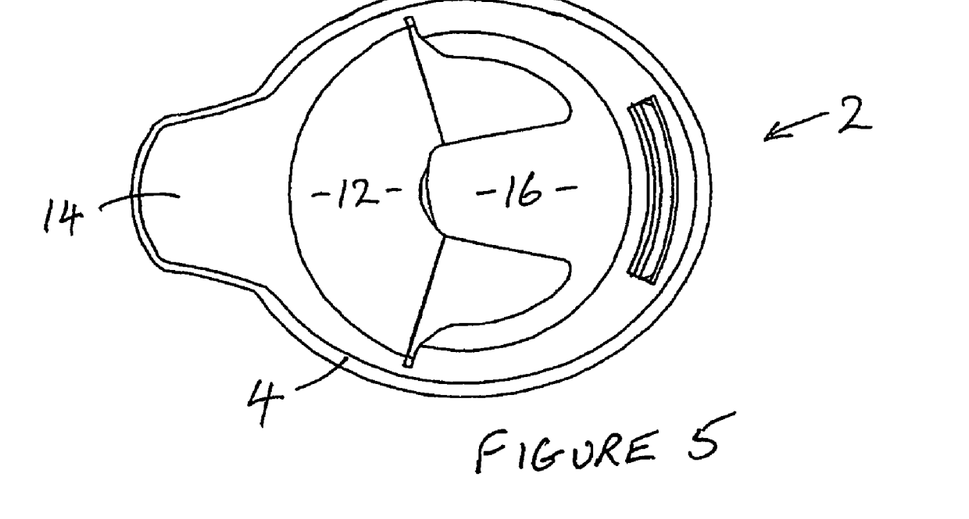
FIG. 5 is a plan view of the sampler of FIG. 1.
Figure 6:
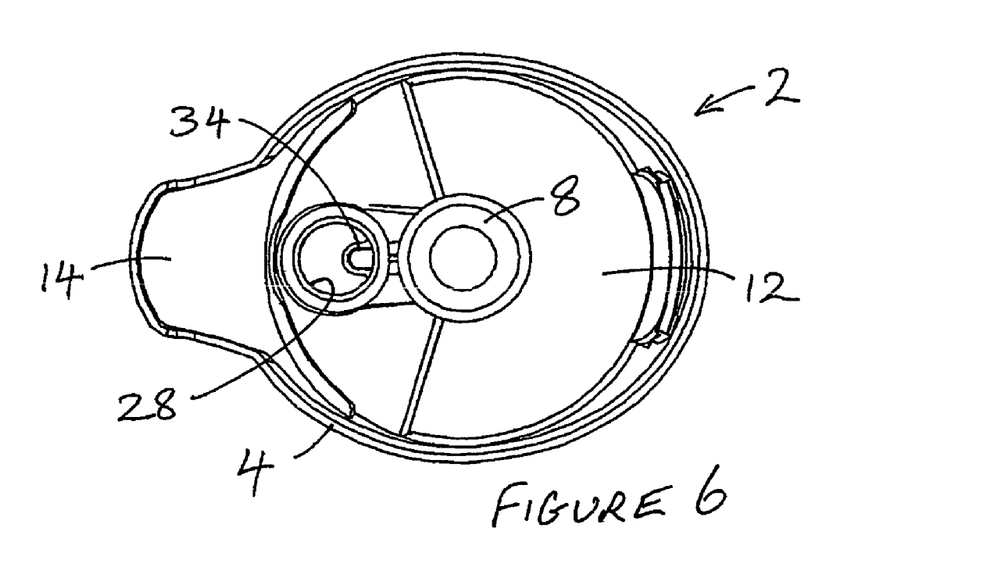
FIG. 6 is a bottom view of the sampler of FIG. 1.
Figure 7:
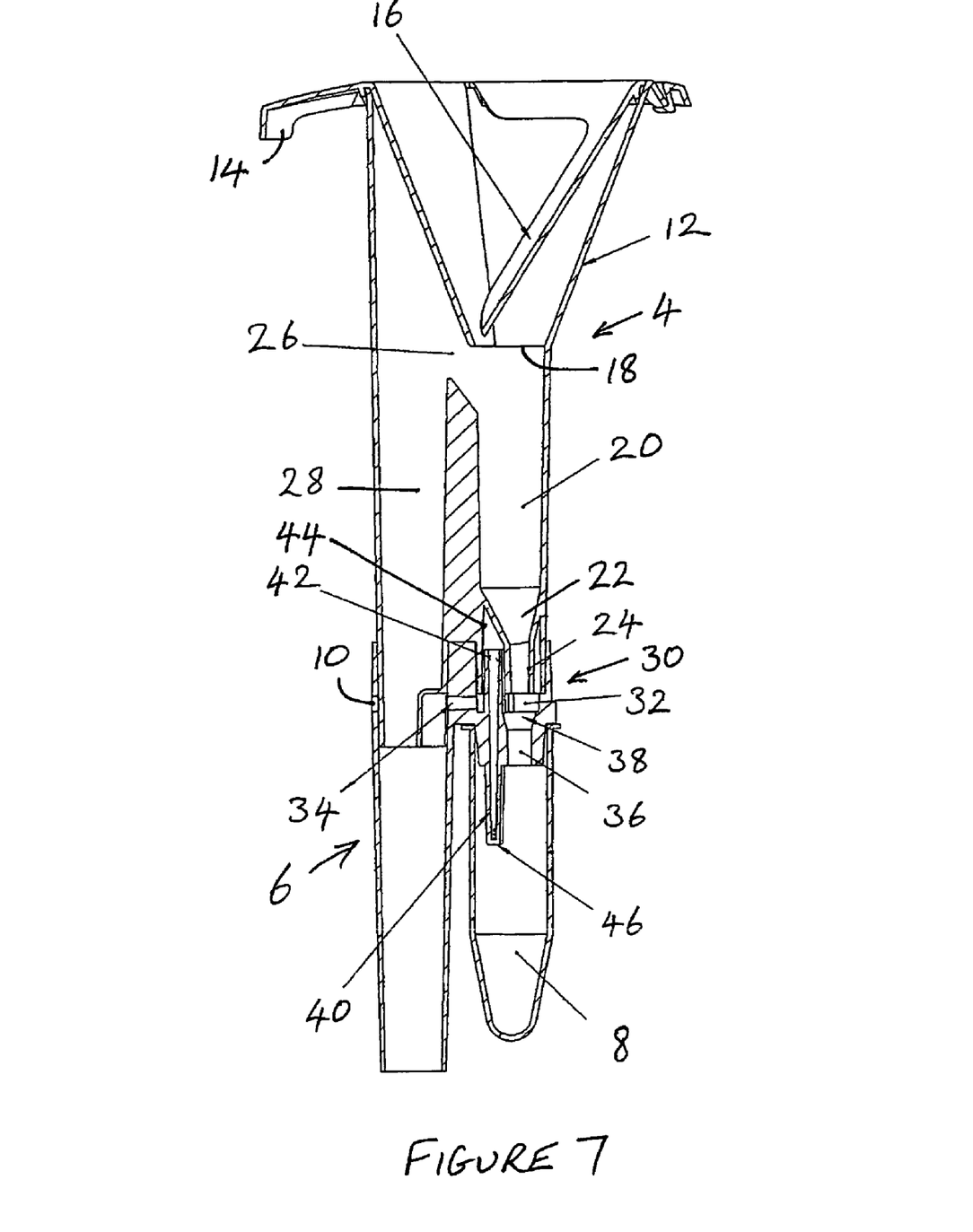
FIG. 7 is a vertical section of the sampler of FIG. 1.
Figure 8:
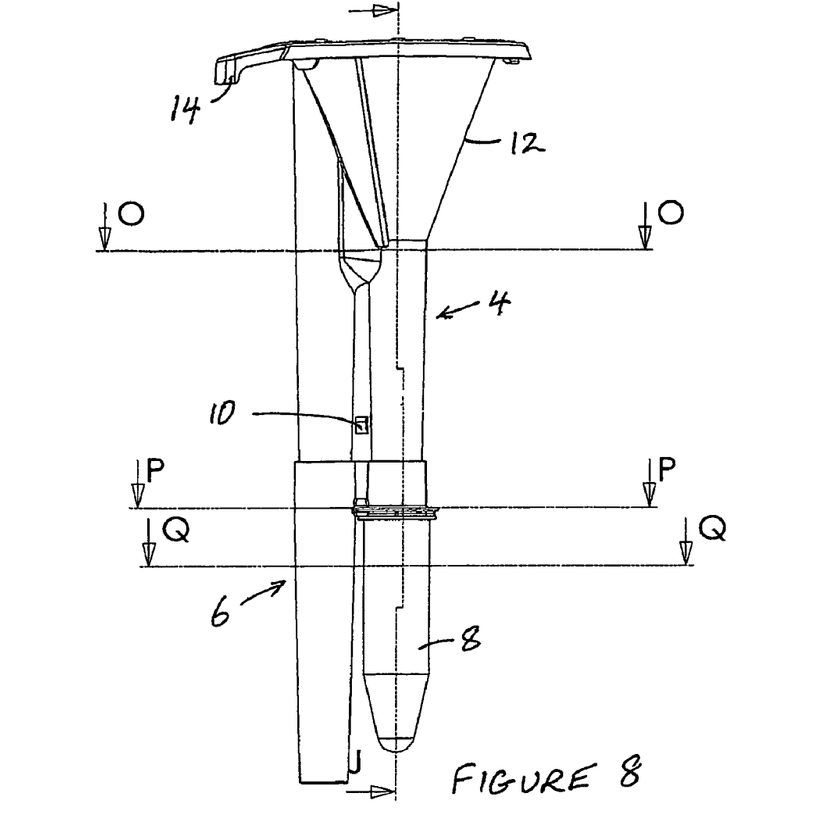
FIG. 8 is a side view of a sampler substantially identical to that of FIG. 1 showing the positions of transverse sections shown in FIGS. 9, 10 and 11.
Figure 9:
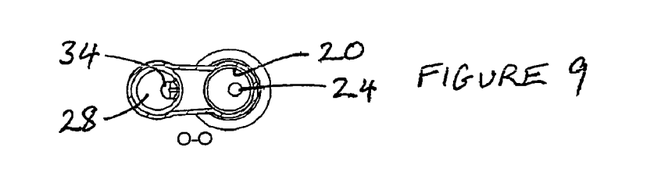
Figure 10:
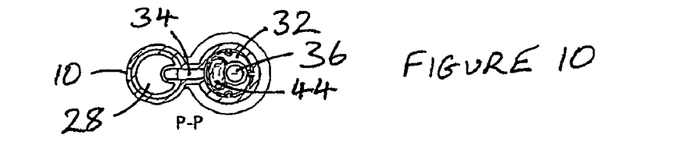

A preferred embodiment provides a urine sampler fabricated from plastic components, as shown in FIGS. 1 to 6 and in section in FIG. 7. A substantially identical sampler, differing only in details of construction, is shown in FIGS. 8 to 11. The samplers of these embodiments are fabricated from machined acrylic. For mass production, it may be preferable to make the sampler by injection moulding and to use a different plastics material suitable for moulding.

The dimensions of the sampler of the embodiment described below have been developed for the acrylic material. If the sampler is fabricated from a different material some modification of the sampler dimensions may be anticipated, particularly if the wetting properties of the material (for the liquid to be sampled) differ significantly from those of acrylic. The principles of operation of the sampler are materials independent, however, and only routine, non-inventive development within the capability of the person skilled in the art would be required to fabricate a sampler from a different material or for a different liquid in the light of the teaching herein.

The sampler 2 comprises an upper portion 4, a valve portion 6 and a sample chamber 8. The valve portion is a push fit onto the lower end of the upper portion, providing a liquid-tight seal, and is retained by a catch 10. The sample chamber is a push fit onto the valve portion, providing a liquid and air-tight seal. The catch ensures that the sample chamber can be removed without accidentally separating the upper and valve portions.

The sampler of the embodiment is designed for use in a substantially vertical orientation, with the sample chamber at the bottom. The following text will describe it in this orientation.

The upper end of the upper portion forms a funnel 12 for receiving urine. A handle 14 is provided for a user to hold the sampler while providing a urine specimen. Within the funnel, a baffle 16 is positioned to modulate the flow of urine and reduce turbulence at the funnel outlet 18. The handle, the baffle and a portion of the funnel may be, moulded as a separate component and fastened onto the remainder of the upper portion by means of a clip 19 for convenience of manufacture.

The funnel outlet 18 drains into a first-catch reservoir 20 within the upper portion of the sampler. The first-catch reservoir is substantially cylindrical except at its lower end, where a frusto-conical tapered section 22 links it to a substantially cylindrical valve inlet 24, which is preferably of circular cross-section. When a urine specimen enters the funnel, it drains into the first-catch reservoir and flows through the valve inlet, in a cylindrical stream out of the upper portion of the sampler. The flow rate is determined primarily by the cross-section and lengths of the valve inlet and the tapered section and the head of liquid in the first-catch reservoir.

Below the level of the funnel outlet and at the upper end of the first-catch reservoir, a main overflow 26 leads to a vertical exhaust passage 28, which extends downwardly, substantially parallel to the first-catch reservoir and the valve inlet.

When the upper portion of the sampler is secured to the valve portion, the valve inlet forms the uppermost component of a valve 30. The structure of the valve can be seen in the sectional views of FIGS. 7, 9, 10 and 11.

At its lower end, the valve inlet leads into a shut-off chamber 32. This chamber is larger than the valve inlet in horizontal cross-section and its side walls are set back from the walls of the valve inlet, so as not to interfere with the flow of urine out of the valve inlet. The shut-off chamber extends horizontally to a shut-off chamber overflow 34, which drains into the exhaust 28.

A tapered passage 38 extends downwardly from the shut-off chamber, leading to a narrower, substantially cylindrical valve outlet 36 which opens into the sample chamber. The valve outlet is aligned with the valve inlet and is preferably circular in section, having a slightly larger diameter than the valve inlet. Thus, in use, a urine stream from the valve inlet can initially pass through the shut-off chamber and the valve outlet without touching the walls of either the shut-off chamber or the valve outlet.

The valve outlet is slightly offset to one side of the sample chamber. This allows space for a vent tube 40 which extends from within the sample chamber, upwardly through the shut-off chamber and opens at its upper end 42 into a vent tube pocket 44. The lower end of the vent tube is blind but one or more vent holes 46 are defined in a side wall of the vent tube near its lower end. The holes preferably do not open either facing towards the centre of the sample chamber and the valve outlet or in the opposite direction towards the closest portion of the sample chamber wall, but open laterally, into or out of the plane of the section in FIG. 7. This reduces the risk of liquid splashing in the sample chamber blocking the vent holes prematurely.

The vent tube is moulded as part of the valve portion of the sampler and, when the sampler is assembled, its upper end enters the vent tube pocket, which is a moulded recess in the upper portion of the sampler. When the sampler is assembled, the vent tube pocket is connected to and extends upwardly from the shut-off chamber, the upper end of the vent tube extending into the pocket alongside the valve inlet 24.

Figure 11:
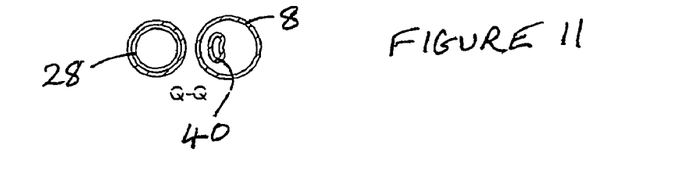

As shown in the transverse section of FIG. 11, the vent tube need not be of circular section but is advantageously of an elongated or arcuate section to maximise the cross-sectional area of the vent while keeping it spaced from the valve outlet and the urine stream passing into the sample chamber. It is advantageous for the sample chamber to vent freely in order to allow the first-void urine to flow as quickly as possible into the sample chamber. This reduces the risk of first-void urine mixing with later portions of the urine specimen in the first-catch reservoir.

Figure 12:
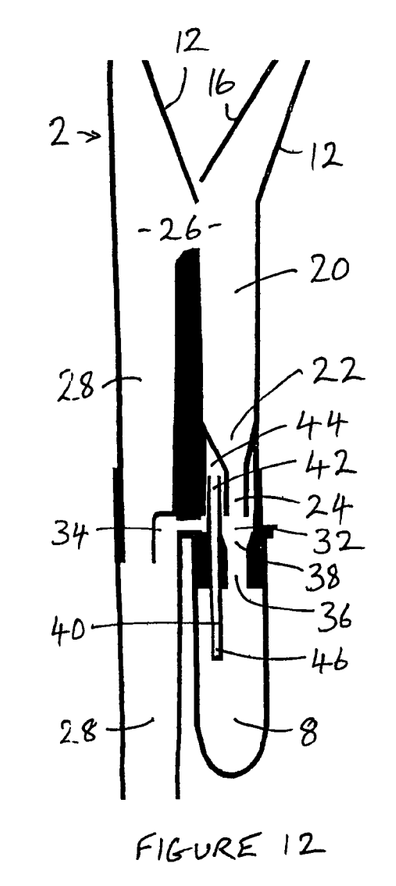
FIGS. 12 to 26 are vertical sections of a central portion of the sampler of FIG. 1 in various stages of urine collection.

FIGS. 12 to 26 illustrate the operation of the sampler of the embodiment during the collection of a first-void urine sample from a urine specimen. Each figure shows the sampler in cross-section, omitting its upper and lower ends in order to focus on the valve operation. Reference numerals identifying components of the sampler are shown in FIG. 12 but have been omitted from FIGS. 13 to 26 for clarity.

Figure 13:
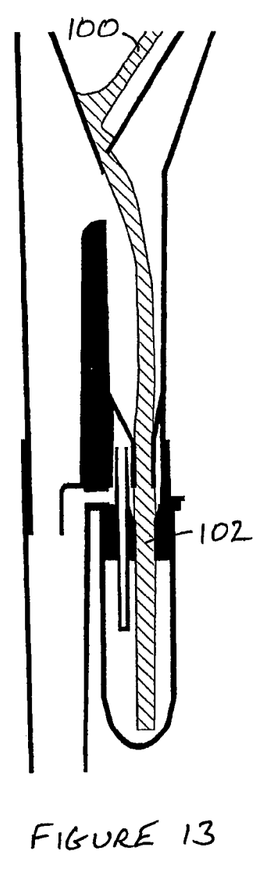

FIG. 13 shows a urine specimen 100 entering the funnel and draining between the funnel and the baffle into the first void chamber. Initially, the urine flows through the valve inlet 24 and passes as a cylindrical column, or jet, 102 into the sampler chamber. The diameter of the urine column, or jet, 102 is determined primarily by the shape and size of the valve inlet and is arranged so that the column passes directly through the shut-off chamber and the valve outlet at this stage.

Figure 14:
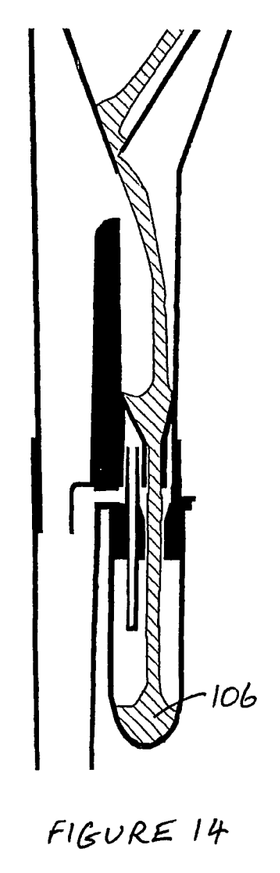
Figure 15:
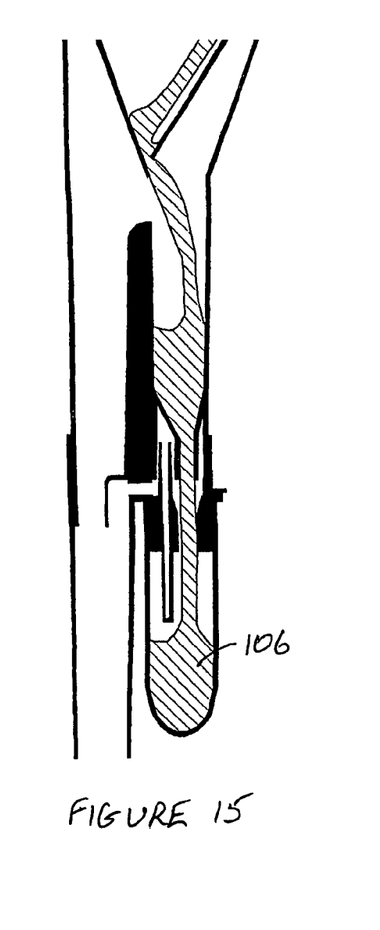
Figure 16:
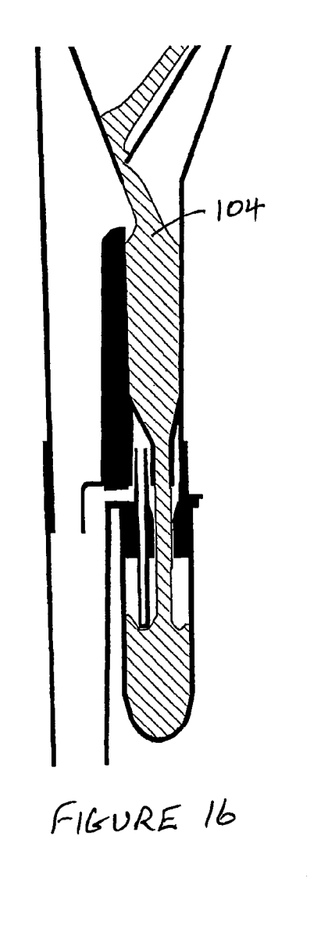

The flow rate through the valve inlet is predetermined to be slower than the flow rate into the funnel and therefore, as shown in FIG. 14, the level of liquid within the first void chamber 20, 22 above the valve inlet begins to rise as shown in FIGS. 14 to 16, until it reaches a level 104 just below the main overflow 26, as shown in FIG. 16. During this time, the liquid level 106 in the sample chamber rises. After this point, as shown in FIG. 17, urine 108 begins to flow into the main overflow and the exhaust 28, preventing the liquid level from rising further within the sampler.

Figure 17:
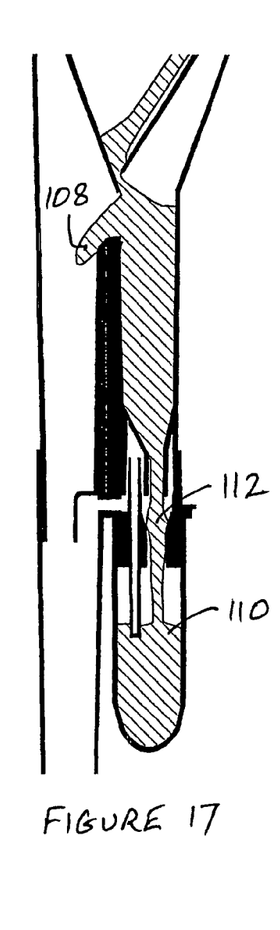

At about this stage, as shown in FIG. 17, the liquid level 110 in the sample chamber rises to cover the vent holes 46 near the end of the vent tube 40. In FIG. 17, this occurs at about the same time that the liquid in the first-catch reservoir overflows through the main overflow. This may not always be the case, however. For example, if the urine specimen is provided more rapidly, the first-catch reservoir will overflow before the liquid level in the sample chamber covers the vent holes.

While the sample chamber is filling, up to the point at which the vent holes are covered, the air displaced from the sample chamber by the liquid passes through the vent holes, along the vent tube, through the vent tube pocket and escapes through the shut-off chamber overflow. When the vent holes are covered, however, air can no longer escape along this route. The only escape route is then upwards through the valve outlet (alongside the column of urine entering the sample chamber) and through the shut-off chamber overflow. As the air in the sample chamber flows up the valve outlet, against the direction of flow of the urine, and the air pressure in the sample chamber rises, the column of urine is disturbed and bulges and touches the walls of the valve outlet. The initial bulging of the urine column is shown at 112 in FIG. 17.

Figure 18:
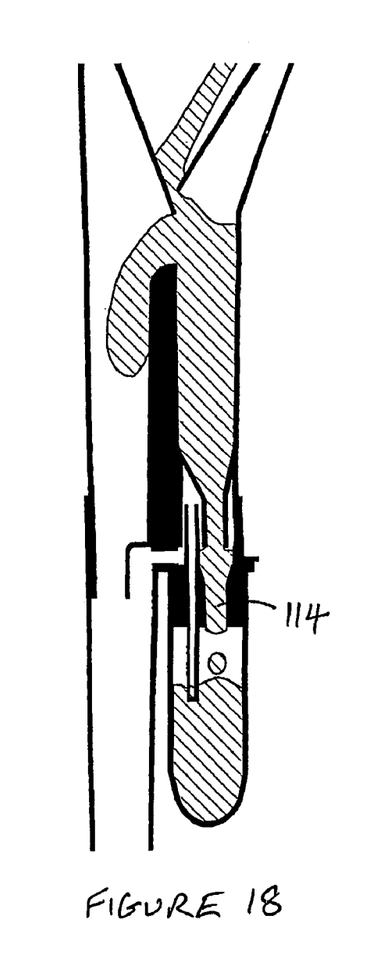

When the urine column wets the valve outlet around its entire circumference, no further air can escape from the sample chamber. The combination of capillary attraction between the urine and the wall of the valve outlet and the increased air pressure in the sample chamber prevents further flow of urine 114 through the valve outlet, as shown in FIG. 18.

Figure 19:
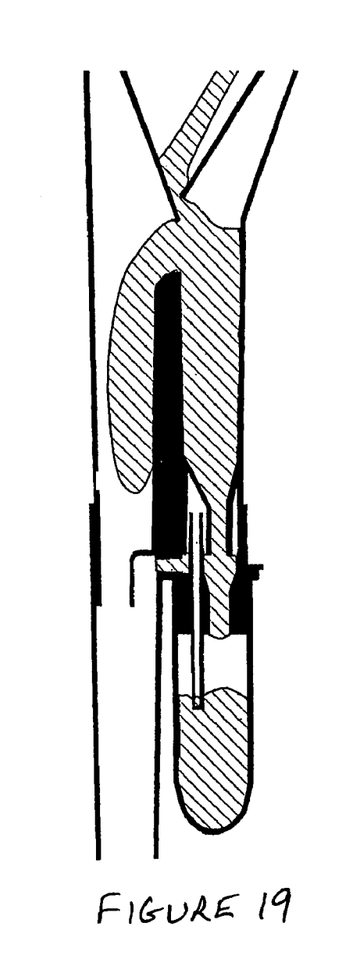
Figure 20:
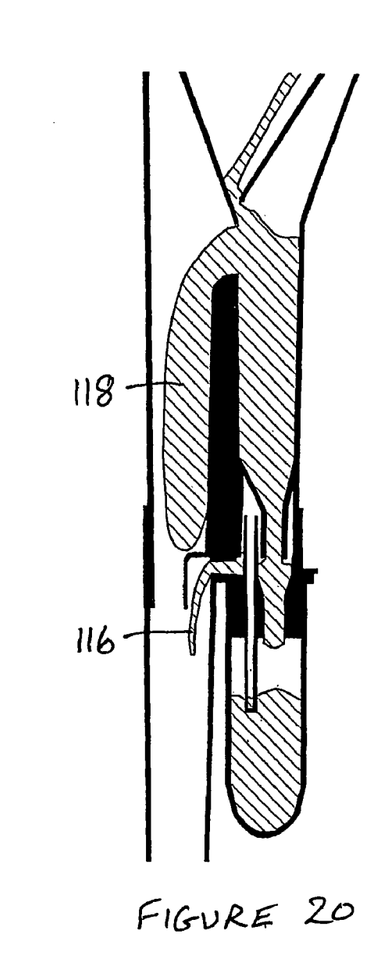

This effectively closes the valve 30. As shown in FIGS. 18 to 20, no further urine enters the sample chamber and the shut-off chamber is filled by urine flowing through the valve inlet from the first-catch reservoir. This liquid covers the lower end of the vent tube pocket, providing a further seal to prevent air leaving the sample chamber. As shown in FIG. 20, this liquid 116 escapes through the shut-off chamber overflow. At the same time, if urine is still entering the funnel, any excess 118 at the top of the catch reservoir escapes through the main overflow.

Figure 21:
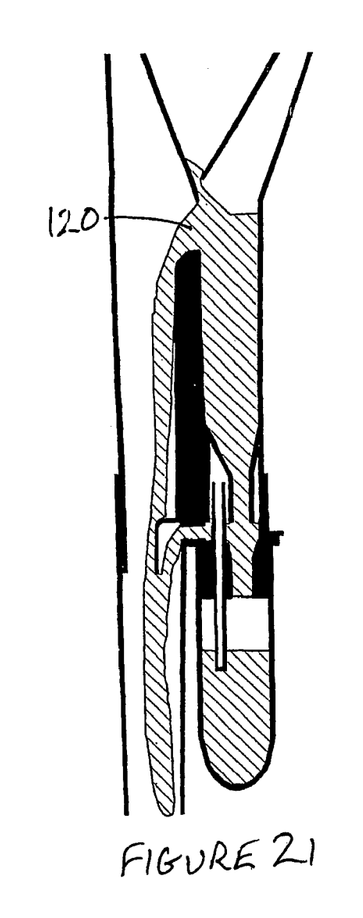
Figure 22:
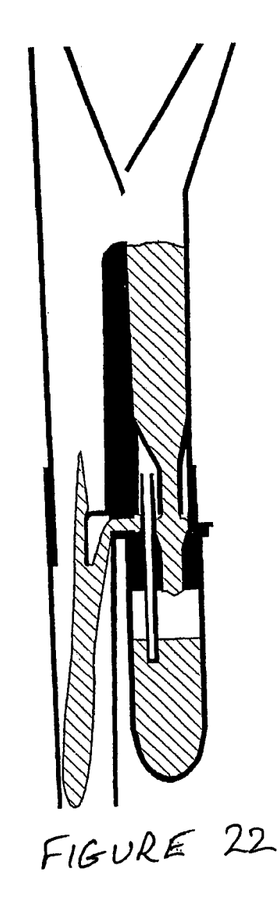
Figure 23:
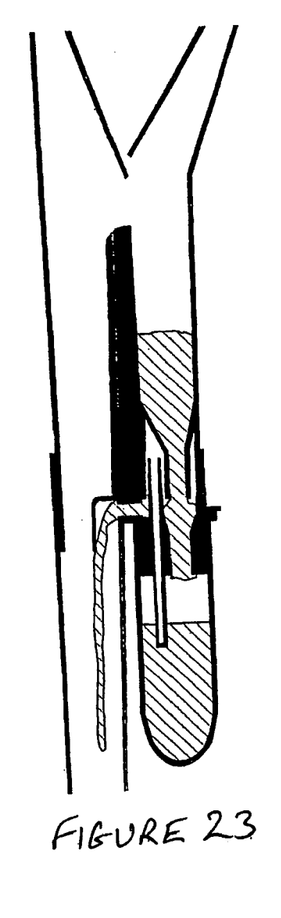
Figure 24:
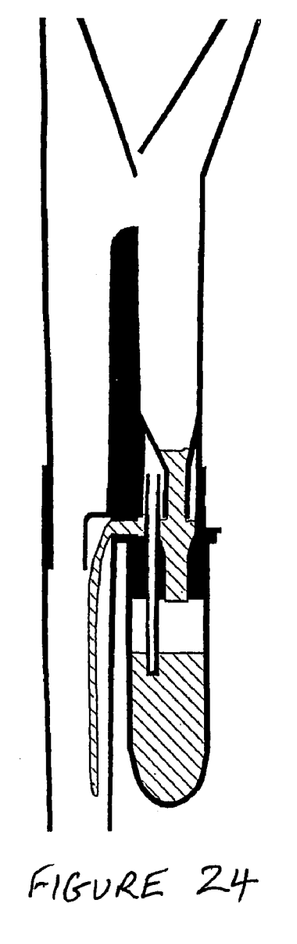
Figure 25:
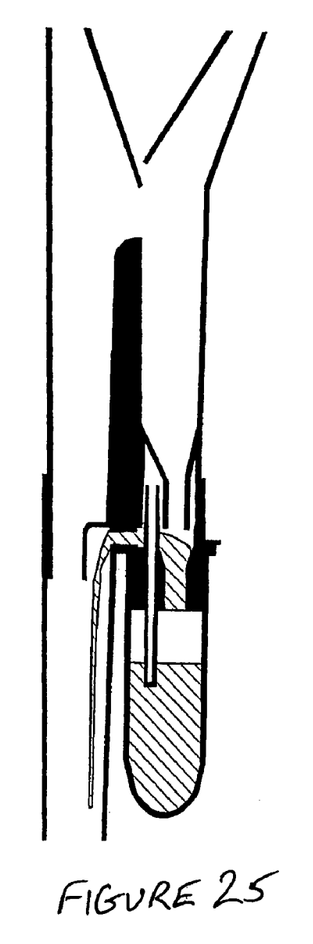
Figure 26:
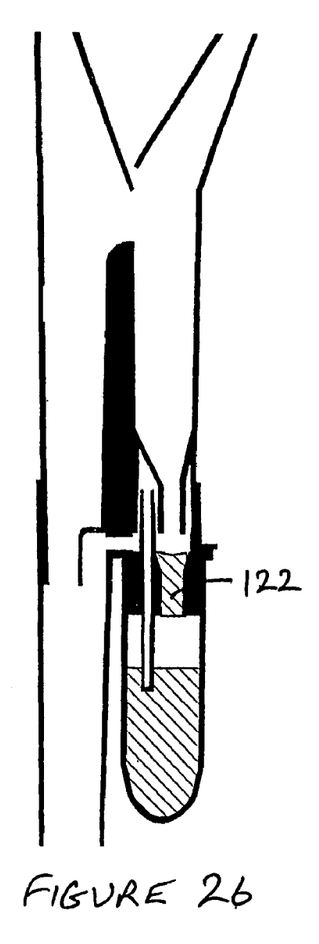

When delivery of the urine specimen into the funnel ceases, as shown in FIG. 21 any liquid 120 above the main overflow drains through the main overflow while liquid in the first-catch reservoir and the shut-off chamber drains through the shut-off chamber overflow. This process continues as shown in FIGS. 22 to 25, until the first-catch reservoir and the shut-off chamber are empty. The final configuration of the sampler is shown in FIG. 26, in which the desired sample is in the sample chamber and a small volume of urine 122 remains in the valve outlet, held by capillary attraction. The sample chamber may then be detached from the remainder of the sampler, without dislodging the liquid 122 within the valve outlet, for analysis or other purposes.

It can be seen that the urine sample in the sample chamber may advantageously contain a large proportion of first-void urine, subsequent parts of the specimen having been directed to the exhaust 28.

It can also be seen that in the final configuration of the sampler, shown in FIG. 26, the sample is securely held within the sample chamber even if the sampler is tilted or inverted. Once the valve outlet is blocked by capillary attraction and the vent holes are covered by the sample, the airlock within the sample chamber may advantageously prevent the sample from escaping either through the valve outlet or the vent tube.

Features and Functions of the Sampler

Funnel 12

The angle of the funnel is selected to encourage efficient flow into the first-catch reservoir. If the funnel angle is too shallow, undesirable mixing of urine in the funnel may occur. However, if the funnel angle is too steep, urine may be forced too quickly into the first-catch reservoir, causing turbulence and mixing in the reservoir.

In the embodiment, the funnel angle, between two opposite walls of the funnel, is 40 degrees.

Baffle 16

The baffle should prevent urine jetting directly into the first-catch reservoir, which would cause mixing, or into the overflow, which would risk losing the first-void urine. The profile of the baffle should be selected to encourage tangential flow, rather than vertical flow, within the sampler, to reduce mixing and encourage flow into the main overflow when the first-catch reservoir has filled. This assists in achieving the object of the sampler, of collecting the first few milliliters of urine in the specimen.

When a urine specimen first enters the sampler, it enters the first-catch reservoir and immediately begins to flow into the sample chamber. The valve inlet restricts the urine flow rate and so, as the sample chamber fills, the urine level in the first-catch reservoir rises. It is therefore desirable to limit mixing of urine in the first-catch reservoir, otherwise later portions of the urine specimen might mix with first-void urine at the lower end of the first-catch reservoir and enter the sample chamber, disadvantageously diluting the sample. The design of the baffle can help to reduce such mixing by encouraging horizontal, rather than vertical, flow directions within the sampler and especially within the first-catch reservoir. Advantageously, limiting vertical flow can lead to layering of the urine in the first-catch reservoir, with more concentrated first-void urine at the bottom, which will flow into the sample chamber, and urine containing a higher proportion of later parts of the urine specimen at the top.

In the embodiment, the clearance between the baffle end and the inside of the funnel should be between 1.5 mm and 3.0 mm. Clearance less than 1.5 mm tends to restrict flow and lead to urine collecting above the baffle, which disrupts flow into the sampler. Clearance more than 3 mm tends to lead to a risk of the urine specimen jetting directly into the main overflow or the first-catch reservoir.

First-catch Reservoir

The reservoir traps the first-void urine however quickly the specimen is delivered and limits mixing with later portions of the specimen, which escape through the main overflow. In practice, about the first 1 ml or 2 ml of the sample enters the sample chamber rapidly, while the first-catch reservoir fills. If the desired sample size is, say, 4 ml, the balance of the sample is contained at that stage in the lower part of the first-catch reservoir, and drains progressively into the sample chamber. FIGS. 13 to 16 illustrate this process in the embodiment. When the first-catch reservoir fills, its upper part contains liquid which is not intended to form part of the sample but which effectively forms a buffer to protect the liquid in the lower part of the first-catch reservoir from turbulence and mixing caused by further urine entering the sampler, and therefore helps to reduce dilution of the sample. This is a facet of the phenomenon of layering discussed above. Thus, the capacity of the first-catch reservoir should advantageously be greater than the desired sample volume minus the volume of the part of the sample which enters the sample chamber before the first-catch reservoir has filled plus the volume of the buffer liquid. In effect, for sample volumes of a few milliliters this means that the capacity of the first-catch reservoir advantageously approximately equals the desired sample volume to be collected.

The diameter of the first-catch reservoir should be selected to prevent or reduce mixing between urine at the bottom of the reservoir and urine higher in the reservoir, which may occur if the diameter is too large. (The issue of mixing and layering in the first-catch reservoir is also discussed above in relation to baffle design). However, if the first-catch reservoir diameter or volume is too small, then a portion of the first-void urine may be lost through the main overflow.

As described above the first-catch reservoir preferably has a minimum volume to prevent dilution of the sample, but it is also desirable that its diameter or cross-section is not too large. There may therefore need to be a compromise between these dimensions in order to prevent the height of the first-catch reservoir, and therefore the height of the sampler, being undesirably large.

In the embodiment, the diameter of the cylindrical portion of the reservoir is 10 mm and its height is 50 mm. This is appropriate for a 4 ml sample volume. For different sample volumes of a few milliliters, the height or other dimensions of the first-catch reservoir may advantageously be varied so that the reservoir volume is about the same as the sample volume.

First-catch Reservoir, Frusto-conical Section 22

This lower section of the first-catch reservoir, which may be termed the reservoir funnel, blends the diameter of the first-catch reservoir down to the diameter of the valve inlet. The angle of the reservoir funnel should be selected as follows. If the angle is too shallow, flow into the valve inlet may be inhibited. If the angle is too steep, it may encourage excessively rapid flow through the valve inlet. In the embodiment, the reservoir funnel is 10 mm in length, blending from the 10 mm diameter of the first-catch reservoir to the 3.2 mm diameter of the valve inlet.

Valve Inlet

In the embodiment, this is a circular cylinder of 3.2 millimeter diameter. This provides a focussed jet, or column, of urine, through the valve outlet into the sample chamber.

The diameter of the valve inlet should not be too small, in which case the jet of urine it produces may puncture through the drop of urine in the valve outlet, which is held by capillary action and prevents further flow into the sample chamber after the sample has been collected.

Tapered Passage 38 Leading to the Valve Outlet

As described above, the urine column from the valve inlet initially passes through the valve outlet directly into the sample chamber. At this stage it is important that the urine flows freely into the sample chamber and so it is desirable to prevent the urine column from wetting the entire circumference of the valve outlet, which might cause formation of a plug of liquid held by capillary action in the valve outlet and prematurely disrupt or prevent further urine flow into the sample chamber.

If the sampler is tilted during collection of a specimen, the urine column produced by the valve inlet may curve downwards. The provision of a tapered entrance to the valve outlet may increase the tolerance of the sampler to being tilted during use by reducing the chance or the extent of contact between the urine column and the circumference of the valve outlet or the floor of the shut-off chamber beside the valve outlet.

Valve Outlet 36

The dimensions of the valve outlet may advantageously be selected in view of the following factors. Its diameter should be small enough to enable the collected sample in the sample chamber to remain sealed by the surface tension in the suspended urine drop, or plug, within the valve outlet. The tapered passage 38 leading into the valve outlet helps to cope with any irregularities in the urine stream exiting the valve inlet, which may arise due to turbulence or tilting of the sampler.

A further factor is the relationship between the sizes and positions of the valve inlet and the valve outlet. In the embodiments described above the valve outlet is aligned with and of slightly larger diameter than the valve inlet. This is one way to achieve the functional requirements of this aspect of the sampler that the urine column from the valve inlet should pass freely through the valve outlet until, at a predetermined liquid level in the sample chamber, the column is disrupted and a plug of liquid forms in the valve outlet, causing further urine to be diverted into the shut-off chamber. Thus, the valve outlet may be of any size or orientation as long as these functional requirements are met; it may, for example, be tilted relative to the valve inlet so that the urine initially strikes and flows along the wall on one side of the valve outlet into the sample chamber.

In the embodiment, the valve outlet is a circular cylinder of 4.2 mm diameter and 8.5 mm long. The tapered passage at its entrance is 3.5 mm long and flares at an angle of 30 degrees.

Vent Holes 46

Each vent hole should be sufficiently small that when the urine level in the sample chamber rises to cover the vent holes, the urine is prevented by surface tension from entering the vent tube. The cumulative cross-section of all of the vent holes (or slots) should be large enough to allow air to escape through the vent tube fast enough to allow the sample chamber to fill; it is desirable to allow the sample chamber to fill sufficiently quickly to prevent unnecessary mixing of the first-void urine in the first-catch reservoir with later portions of the urine specimen.

It may be advantageous to use slot-shaped vent holes, rather than circular vent-holes for example, to increase air flow while reducing the minimum lateral dimension of the vent-holes and therefore making it easier for surface tension to block the vent-holes.

In the embodiment, the maximum dimension for any one of the vent holes is 0.5 mm, to prevent urine ingress into the vent tube, and the minimum total open area of all of the vent holes is 0.8 mm$^2$, to provide sufficient air flow rate.

Vent Tube 40

As described above, the lower end of the vent tube in the embodiment may be sealed and vent holes advantageously defined in the side of the vent tube near its end and on the side of the vent tube facing neither the urine column entering the sample chamber nor the wall of the sample chamber furthest from the entering urine column. When the urine enters the sample chamber, it tends to splash, rising particularly high adjacent the wall of the sample tube furthest from the valve outlet. This is driven by the tendency of the urine stream to rotate at the bottom of the sample tube, following the wall of the sample chamber. The positioning of the vent holes on the sides of the vent tube therefore helps to control unwanted or premature splashing of the vent holes.

The upper end of the vent tube nests into the vent tube pocket. It should be noted that when the shut-off chamber floods after collection of the sample in the sample chamber, the lower end of the pocket is sealed by the presence of the urine, which helps to maintain the air pressure within the sample chamber, which in turn prevents further access of urine into the sample chamber.

In the embodiment, the vent pocket wall is spaced from the vent tube by between 0.25 mm and 0.5 mm.

Shut-off Chamber 32

The height of the shut-off chamber determines the distance between the valve inlet and the valve outlet, and so may affect the relationship between their diameters. The capacity of the shut-off chamber also affects how quickly and effectively the vent pocket is sealed after the sample is collected. Further, the height of the shut-off chamber affects the tolerance of the sampler to tilting during use, given that the urine stream leaving the valve inlet must pass through the shut-off chamber and the valve outlet as described above.

If the shut-off chamber volume is too large or its height is too great, then after urine stops flowing into the sample chamber and starts flowing into the shut-off chamber, it may take too long to reach and cover the vent-tube pocket. This may lead to unreliability as, until the vent-tube pocket is covered, the sealing of the sample chamber depends on the plug of liquid in the valve outlet and the capillary action sealing the vent holes. If the shut-off chamber volume is too small or its height too small, then if the urine column flowing from the valve inlet accidentally hits the edge of the valve outlet within the shut-off chamber, sufficient liquid may collect in the shut-off chamber to cover the vent-tube pocket and cause the valve to close prematurely. Again, this is a reliability issue, which may lead to inconsistent operation if, for example, the sampler is tilted or shaken excessively during urine collection.

It will be appreciated that other features such as the tapered entrance passage of the valve outlet may also affect these aspects of the sampler's operation; the shape and size of the tapered passage influence the risk of the urine column hitting the floor of the shut-off chamber adjacent the edge of the valve outlet (or its tapered entrance passage) and prematurely deflecting liquid into the shut-off chamber.

In the embodiment, the shut-off chamber is 3.5 mm high and has a volume of approximately 320 mm$^3$.

Shut-off Chamber Overflow 34

This overflow allows urine from the shut-off chamber to escape to the exhaust passage. The cross-section of the overflow must not be too large, otherwise it will empty the shut-off chamber too quickly, which could break the seal provided by the urine in the shut-off chamber at the base of the vent pocket. If the shut-off chamber overflow is too small, it may not allow sufficient flow through the shut-off chamber to block the vent pocket quickly enough when the sample chamber is filled to the required level.

In the embodiment, the shut-off chamber overflow is a circular cylindrical passage of diameter 2.4 mm.

Sampler Characteristics

The sampler of the embodiment is designed to collect a 2 ml sample. It is designed to operate at urine flow rates between 15 ml and 30 ml per second. For other applications, the sizes of the components of the sampler may be altered appropriately, for example to collect samples of 5 ml or 10 ml. It is desirable that the sample should be as pure as possible, ideally containing only the desired volume of first-void urine. Usually, however, some dilution of the sample with later portions of the urine specimen occurs due to mixing in the first-catch reservoir. Tests have, for example, achieved collection of 10 ml samples in which each sample was collected from amongst the first 12 ml of the (much larger) urine specimen.

For reliable operation, it is important that the internal surfaces of the sampler are clean and dry because wetting of components such as the valve outlet and the shut-off chamber should be predictable. In one embodiment, the sampler may be manufactured as a disposable item and kept in a sealed container before use, ensuring that it is clean and dry when used. If a sampler were to be reused, it may be important to be able to dismantle it for effective cleaning and drying.

Further Embodiments

In a simpler embodiment, the sample chamber is not provided with a vent-tube extending into the chamber, while the valve outlet is lengthened by a tubular portion extending into the sample chamber. While the sample chamber is filling, the liquid column from the valve inlet passes through the valve outlet and air from the chamber vents through the valve outlet alongside the liquid column. When the urine level in the sample chamber reaches the end of the urine valve outlet, no further air can escape and the liquid column in the valve outlet is disrupted, wetting the circumference of the valve outlet and forming a liquid plug. This closes the valve, diverting the urine flowing from the valve inlet into the shut-off chamber and through the shut-off chamber overflow.

The invention claimed is:

1. A sampler for sampling a first portion of a liquid flow, comprising an upper portion, a valve portion, and a sample chamber, wherein the upper portion comprises a sample inlet and the valve portion comprises:

a valve inlet coupled to the sampler inlet;
a valve outlet opening into the sample chamber, wherein the valve outlet is positioned substantially below the valve inlet;
a vent tube extending between the vent inlet and the vent outlet, wherein the vent inlet is positioned within the sample chamber and the vent outlet is positioned at a level above the valve outlet;
a shut-off chamber separating the valve inlet from the valve outlet; and
a shut-off chamber overflow-comprising a valve overflow leading out of the shut-off chamber,
wherein the liquid flow enters the upper portion, passes through the sampler inlet and valve inlet into the valve portion, and the first portion of the liquid flow passes through the valve outlet into the sample chamber.

2. A sampler according to claim 1, wherein the valve outlet has larger transverse dimensions than the valve inlet.

3. A sampler according to claim 1, wherein the valve outlet is aligned with the valve inlet.

4. A sampler according to claim 1, wherein the level of the vent inlet within the sample chamber determines the level of liquid to be collected within the sample chamber, and further wherein the valve closes when liquid in the sample chamber reaches the vent inlet and obstructs it, substantially preventing further venting of air from the sample chamber.

5. A sampler according to claim 1, wherein the vent outlet opens into a vent-tube pocket which extends upward from the shut-off chamber.

6. A sampler according to claim 1, wherein after the first portion of the liquid flow is collected in the sample chamber, further liquid flow entering the valve during use drains through the valve overflow.

7. A sampler according to claim 1, wherein the sampler inlet comprises a first-catch reservoir opening into the valve inlet.

8. A sampler according to claim 7, wherein the sampler inlet further comprises a main overflow positioned at an upper end of the first-catch reservoir.

9. A sampler according to claim 8, wherein the shut-off chamber overflow and the main overflow lead into a common overflow outlet of the sampler.

10. A sampler according to claim 7, wherein the upper portion further comprises an entrance funnel opening into the first-catch reservoir.

11. A sampler according to claim 10, wherein the funnel comprises a baffle for reducing turbulence within the first-catch reservoir.

12. A sampler according to claim 1, wherein the sample chamber is removable.

13. A liquid sampler according to claim 1, further comprising a collection means for collecting further liquid flow after the first portion of the liquid flow has been collected in the sample chamber.

14. A liquid sampler according to claim 1 for sampling a first-void urine sample when a flow of urine is introduced into the upper portion.

15. A first-void urine sampler of claim 14, wherein the first-void urine sample is collected in the sample chamber and later-voided urine is diverted away from the sample chamber.

16. A first-void urine sampler of claim 14, further comprising a collection means for collecting later-voided urine.

17. A method for sampling a first portion of a liquid flow using a sampler of claim 1, wherein:

liquid flow is introduced into the upper portion of the sampler;

the liquid flow enters the sampler inlet and passes through the valve inlet into the valve portion;

a first portion of the liquid flow passes through the shut-off chamber and valve outlet of the valve portion and enters the sample chamber;

the first portion of the liquid flow is collected in the sample chamber until it reaches a predetermined level at which further liquid flow through the valve outlet into the sample chamber is blocked; and further liquid flow into the valve portion of the sampler is diverted through the shut-off chamber and drains through the shut-off chamber overflow.

18. A method according to claim 17, wherein the predetermined level is at an exit of the valve outlet.

19. A method according to claim 18, wherein the first portion of the liquid flow collected in the sample chamber reaches the predetermined level and then covers the exit of the valve outlet, such that further liquid flow is diverted through the shut-off chamber and drains through the valve overflow.

20. A method for collecting a portion of a liquid flow, the portion being other than a first portion of the liquid flow, using a sampler according to the method of claim 17, further wherein the further liquid flow diverted through the shut-off chamber overflow is collected.

21. A method according to claim 17, using a sampler which further comprises a first-catch reservoir opening into the valve inlet, and a main overflow positioned at an upper end of the first-catch reservoir, comprising:

introducing liquid flow into the first-catch reservoir until the first-catch reservoir is full; draining excess liquid flow through the main overflow when the first-catch reservoir is full;

allowing the liquid in the first-catch reservoir to pass through the valve portion into the sample chamber until the liquid in the sample chamber reaches a predetermined level at which further flow through the valve outlet into the sample chamber is blocked; and after further liquid flow into the sample chamber is blocked, draining any liquid remaining in the first-catch reservoir through the valve inlet into the shut-off chamber and through shut-off chamber overflow.

22. A method according to claim 21, using a sampler which further comprises a first-catch reservoir leading into the valve inlet and a main overflow positioned at an upper end of the first catch reservoir, wherein liquid flow is introduced into the upper portion of the sampler and passes into the first-catch reservoir, and when the first-catch reservoir is full, any further liquid flow introduced into the reservoir is drained through the main overflow.

* * * * *